United States Patent
Banter (10) Patent No.: US 11,408,820 B1
(45) Date of Patent: Aug. 9, 2022

(54) PRODUCE FRESHNESS SENSOR

(71) Applicant: C. Bruce Banter, Northville, MI (US)

(72) Inventor: C. Bruce Banter, Northville, MI (US)

( * ) Notice: Subject to any disclaimer, the term of this patent is extended or adjusted under 35 U.S.C. 154(b) by 0 days.

(21) Appl. No.: 17/688,197

(22) Filed: Mar. 7, 2022

Related U.S. Application Data (63) Continuation-in-part of application No. 63/197,539, filed on Jun. 7, 2021, and a continuation-in-part of application No. 63/188,125, filed on May 13, 2021.

(51) Int. Cl.
| | |
|---|---|
| *G01J 3/46* | (2006.01) |
| *G01N 21/27* | (2006.01) |
| *G01N 21/84* | (2006.01) |
| *G01N 33/02* | (2006.01) |

(52) U.S. Cl.
CPC .......... *G01N 21/27* (2013.01); *G01N 21/84* (2013.01); *G01N 33/025* (2013.01); *G01N 2021/8466* (2013.01); *G01N 2201/062* (2013.01)

(58) Field of Classification Search
CPC ...... G01N 21/27; G01N 21/84; G01N 33/025; G01N 2021/8466; G01N 2201/062
USPC ....................................................... 356/402
See application file for complete search history.

(56) References Cited

U.S. PATENT DOCUMENTS

| | | | | |
|---|---|---|---|---|
| 2004/0148117 A1* | 7/2004 | Kirshenbaum | ........ | G01K 1/022 702/82 |
| 2006/0247967 A1* | 11/2006 | Prusik | .................. | G01N 31/229 705/14.4 |

* cited by examiner

*Primary Examiner* — Md M Rahman
(74) *Attorney, Agent, or Firm* — Gerald R. Black, Esq.

(57) ABSTRACT

A produce freshness sensor inexpensive enough to be discarded after each produce use, and multi-functional that is affixed to the produce by the grower that monitors parameters that affects produce freshness (to measure color and chemical composition), the sensor being used throughout the produce distribution system. A sensor monitors produce freshness and comprises one or more emitters, a temperature sensor, a microprocessor, and a transceiver mounted on a printed circuit board. The sensor is affixed relative to the produce. Power usage is critical to prolong operational time of the temperature sensor. Data collection and transmission are controlled to minimize run time and power usage. An initial baseline is established when the sensor is affixed relative to the produce, the start time and baseline measurements being recorded relative to the baseline. The real-time information is subsequently processed to provide analysis and relevant data to users throughout the produce distribution system.

25 Claims, 10 Drawing Sheets

Healthy plants REFLECT a large amount of near-infrared (NIR) light.
Unhealthy plants ABSORB more near-infrared (NIR) light.

FIGURE 5
The Vegetation Spectrum in Detail

FIGURE 6A
FIGURE 6B
FIGURE 6C (VIEW W/O ENCAPSULATION)
FIGURE 6D (VIEW W/O ENCAPSULATION)
FIGURE 6E (VIEW W/O ENCAPSULATION)

110 - Produce Freshness Sensor
12a and 12b - Sensor Encapsulation
15 - Antenna and Temperature Probe Extension
20 - Printed Circuit Board
30 - Microprocessor
40 - RF Transceiver
50 - Analog Front End/ LED Driver
61 - Light Guide and Emitter #1
62 - Light Guide and Emitter #2
64 - Receiver
72 - Power Source
74 - Power Clip

FIGURE 8
Functional Block Diagram

FIGURE 9

PRODUCE FRESHNESS SENSOR

CROSS-REFERENCE TO RELATED APPLICATIONS

This Application is a continuation-in-part of and claims priority to U.S. Provisional Application No. 63/188,125, entitled "Produce Freshness Sensor" (C. Bruce Banter), filed on May 13, 2021; and U.S. Provisional Application No. 63/197,539, entitled "Wheal and Flare Analyzing System" (C. Bruce Banter), filed on Jun. 7, 2021.

FIELD OF THE INVENTION

The invention relates to a sensor that monitors the freshness of fruits and vegetables in a produce distribution system, the principal properties being monitored are freshness, location, time, temperature, and ripeness, the purpose being to provide fresher and healthier produce for the consumer.

BACKGROUND OF THE INVENTION

The health benefits of the regular consumption of fresh produce (fresh fruits, fresh vegetables, and fresh grains) are well known. Health-conscious consumers are increasingly searching for value-added fresh produce.

Produce providers are challenged to economically deliver high quality and aesthetically pleasing produce to consumers. The cost of produce to the consumer has historically increased very little and small profit margins require cost effective methods. Produce that is rejected for poor quality or recalled for contamination results in cost absorbed by the produce providers. Managing the environmental conditions and time duration during the entire process from farm to grocery shelf is critical.

The information that can be utilized to manage the process are time from harvesting, produce color, environmental and produce temperature, environmental humidity, and ambient ethylene gas content. The cost to create the information versus the value or benefit the information creates drives the implementation and adoption.

Location and timing information is recorded from the initial phases and follows the produce by printed labels or barcodes attached to the produce containers or packaging. The information is manually read or scanned at phase of the process. The best systems would have the location and time information available to the various providers of the supply chain to manage the flow of produce. Electronic location trackers have been available for some time but are expensive and not used in the produce industry. Consumers experience the time information as "best by" dates or expiration dates.

Color is used as a gage of the ripeness and quality of produce but chemical composition such as water content, sugar, and ethylene are also important factors. The visual appearance of produce and the judgment of ripeness is not driven by a single color. The presence of other colors like brown spots and discoloration are an indication of the ripeness process. The color of bananas and pineapples are an example of a metric used to judge the ripeness progress. Ripening guides are used to manage the delivery and supply to the point of sales and on the retail shelf. Consumers typically regard produce beyond the ripe color as poor quality. Retailers now must visually check the produce at delivery and at their point-of-sale shelf.

Produce is harvested at ambient temperatures and conditions and colder temperature are typically introduced after harvesting to slow the ripening process and prolong the useful life of the produce. Temperatures higher or lower than the desired temperature has a detrimental effect on the produce. Monitoring and controlling the temperature of produce all through the delivery process is critical to providing quality produce to consumers. Temperature measurements are done of the space around the produce and preferrable on the produce directly. The actual temperature of the produce can vary greatly from the surrounding temperature because of the density of packing the produce, location within the container, air flow within the space, and internally generated heat from the ripening produce. Temperature measurements of the container or room are only a general indication of the temperature the actual produce has experienced.

Direct temperature measurements of produce is the most useful information but is currently more costly and labor intensive, requiring placement of the measuring equipment and recording the data. Measurements are taken at only a few delivery points throughout the food distribution system because of cost and limitations of the equipment. Currently the following types of temperature sensors are being used:

- Hand-held probes that are inserted into the produce and the measurements are manually or automatically recorded. These probes are retained at the facility and do not travel with the produce.
- Multi-use sensors that are placed in the cartons and retrieved later and reused. This equipment is expensive and only travels within the owner's part of the delivery system.
- One-time-use sensors that store the measurements and provide the information when cooperatively engaged with a computer. These sensors are expensive and are not currently used in the produce industry.
- One-time-use temperature recording labels that change color when the temperature changes. These labels are expensive and are not currently being used in the produce industry.

Control of the humidity of the space around the produce is important to the proper ripening process. Increased humidity can also be a result of the ripening process. Humidity measurement can be an indicator of the ripening process but is being done infrequently because of the cost to generate the information. Humidity measurements are limited to containers and large packages of produce.

Ethylene gas is a byproduct of the ripening process and is also externally introduced to quicken the ripening process. The gas levels are monitored and controlled in ripening chambers. Methods to measure the ethylene gas at the produce have come down in cost recently but are still too expensive to enable monitoring through the entire process.

Evaluations of the produce for temperature and ripeness are done visually and manually recorded at a few points during the process but the information sharing is limited and does not track the produce.

In addition, there is prior art involving the monitoring of produce at point-of-sale.

U.S. patent application Ser. No. 16/594,364 (Bogolea; et al.) discloses a method for tracking fresh produce in a market. The computer system can then detect produce units located in the wrong locations throughout the store (e.g., in unassigned produce displays) and automatically prompt associates to correct such incorrectly placed produce units or distinguish overripe or spoiled produce units from underripe and ripe produce units and automatically prompt associates to discard or replace such overripe or spoiled produce units. The method includes accessing a first hyper-spectral image of a produce display in a store recorded at a first time, extracting a first spectral profile from a first region of the first hyper-spectral image depicting a first set of produce units in the produce display, identifying a first varietal of the first set of produce units, characterizing ripeness, bruising, spoilage of the first set of produce units in the produce display based on the first spectral profile, and in response to qualities of the first set of produce units in the produce display deviating from a target quality range assigned to the first varietal, generating a prompt to audit the first set of produce units in the produce display.

U.S. patent application Ser. No. 14/059,441 (Minvielle) discloses a logistic transport system for storage and logistic transport of nutritional substances. The preservation system obtains information about the nutritional substance to be preserved, senses and measures the external environment to the preservation system, senses and measures the internal environment to the preservation system, senses and measures the state of the nutritional substance, and stores such information throughout the period of preservation. Using this accumulated information, the preservation system can measure, or estimate, changes in nutritional content (usually degradation) during the period of preservation. Additionally, the preservation system can use this information to dynamically modify the preservation system to minimize detrimental changes to the nutritional content of the nutritional substance, and in some cases actually improve the nutritional substance attributes.

The known methods are generally expensive to use, are limited as to measurements taken, and do not enable real-time measurements throughout the entire produce distribution system.

As the produce industry and the general-public clamor for produce that maintains its fresh-picked properties, the produce needs to be processed in a manner safe for workers and consumers alike in a way that is economically feasible.

What is needed is a sensor that can be affixed to the produce by the grower, which is inexpensive enough to be disposed of after travel through the system, which monitors multiple parameters that affect freshness of the produce (to measure the color and ripeness with light) and follows the produce throughout the produce distribution system until the produce ultimately reaches the consumer.

SUMMARY OF THE INVENTION

The produce freshness sensor of the present invention addresses these needs.

As used herein, the term "produce distribution system" includes growers and producers, farms, greenhouses, and ranches, food factories and processing facilities, food storage facilities, food transporters, markets, grocery stores and retail outlets.

As used herein, the term "affixed relative to" includes adhered to, pasted to, packaged with or onto, strapped to, attached to, or inserted with.

The produce freshness sensor of the present invention is used throughout the produce distribution system initially by the growers, then by the distributors and the logistic companies, and finally by the retailers.

As used herein the word "produce" includes all fruits and vegetables. Produce is a generalized term for many farm-produced crops, including fruits and vegetables (grains, oats, etc. are also considered produce). More specifically, the term produce often implies that the products are fresh and generally in the same state as when harvested. Anything that grows on a plant and is edible is considered as produce herein, unless clearly the context suggests another interpretation.

As used herein a light guide is a device designed to transport light from a light source to a point at some distance with minimal loss. Light is transmitted through a light guide by means of total internal reflection. Light guides are usually made of optical grade materials such as acrylic resin, polycarbonate, epoxies, and glass.

The produce freshness sensor of the present invention comprises one or more emitters, a microprocessor, a transceiver, and a temperature sensor mounted on a printed circuit board. The produce freshness sensor of the present invention monitors characteristics pertaining to produce freshness as the produce moves through the produce distribution system. The produce freshness sensor of the present invention is affixed relative to the produce. The produce freshness sensor of the present invention provides information in real time relative to location, time, temperature, and ripeness of the produce.

The real-time information is transmitted by wireless communication to a cloud. Real-time information analysis and relevant data are provided to users throughout the produce distribution system. The produce freshness sensor of the present invention monitors characteristics pertaining to produce freshness as the produce moves through the produce distribution system. The produce freshness sensor of the present invention provides information in real time relative to location, time, temperature, and ripeness of the produce.

An initial baseline is established when the sensor is affixed relative to the produce, the start time and baseline measurements being recorded relative to the baseline.

Power usage is critical to prolong operational time of the produce freshness sensor. The produce freshness sensor of the present invention is kept in a low power or sleep state most of the time. Sensor on-time of the temperature measurements, ripeness measurements and transmission of data to the cloud are managed to conserve the stored energy. The stored power from a battery or supercapacitor can utilize optional energy harvesting to increase the operational time.

In another preferred embodiment of the produce freshness sensor of the present invention, the sensors are refurbished after completing a cycle through the produce distribution system. The power supply is replaced after disassembly of the sensor or rechargeable power supplies are incorporated and recharged before placing the sensors back in use. Full testing and certification of the sensors are completed before reuse.

The temperature sensing is accomplished by either an analog temperature sensitive resistor (thermistor), or a digital temperature integrated circuit, or by the temperature function in the RF Transceiver. The digital temperature integrated circuits (IC) are more accurate but are also more expensive. The temperature measurement from the RF Transceiver is the lowest cost method but is not as indicative of the ambient temperature as the Temperature IC. The temperature generated by the RF transceiver would add to the ambient temperature and would require compensation to deduce the produce temperature.

The temperature sensor probe and antenna preferably extend beyond the printed circuit board and encapsulation to improve temperature sensing and wireless transmission.

An additional use case for the freshness sensor for the monitoring of the growth and health of vegetation such as grapes on vines and fruit on trees or shrubs. The produce freshness sensor of the present invention is attached to the plant and provides continuous real-time information on the plant. The continuous temperature and ripeness information assist management of the plants. Peak ripeness is detected and communicated as well as stress alerts. A larger power supply or energy harvesting will extend the life of the sensor.

Still other objectives of the processes for produce freshness sensor of the present invention will become apparent to those skilled in this art from the following description wherein there is shown and described in the preferred embodiment of this invention, simply by the way of illustration of the best modes contemplated for carrying out the present disclosure. As will be realized, the present disclosure is capable of different embodiments, and its several details are capable of modification in various, obvious aspects all without departing from the invention. Accordingly, the drawings and descriptions will be regarded as illustrative in nature and not as restrictive.

DETAILED DESCRIPTION OF THE PREFERRED EMBODIMENTS

Figures 1A, 1B:
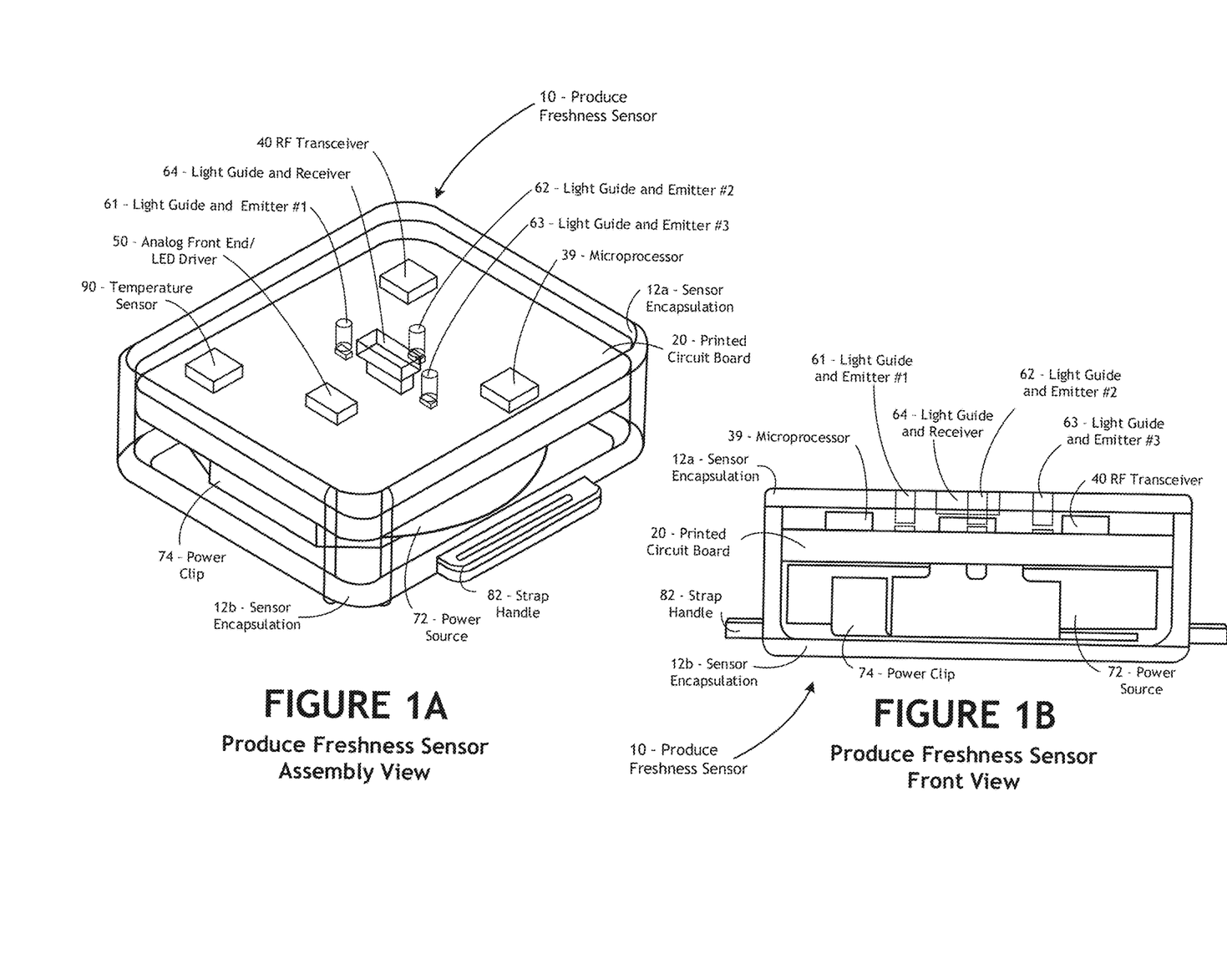
FIG. 1A depicts an assembly view of the first preferred embodiment of the produce freshness sensor of the present invention, including a microprocessor, temperature sensor, an analog front end/LED driver, three light guides and emitters, an rf transceiver, a light guide and receiver, and a power supply all mounted relative to a printed circuit board and encapsulated, the sensor including a strap for ease of mounting relative to the produce.
FIG. 1B depicts a front view of the produce freshness sensor of FIG. 1A.

Referring now to the drawings, FIG. 1A depicts an assembly view and FIG. 1B depicts a front view of the first preferred embodiment of the produce freshness sensor [10] of the present invention. The produce freshness sensor [10] includes a microprocessor [39], temperature sensor [90], an analog front end/LED driver [50], three light guides and emitters [61, 62, and 63], an rf transceiver [40], a light guide and receiver [64], and a power source [72] all mounted relative to a printed circuit board [20] and encapsulated [12a and 12b].

The produce freshness sensor [10] includes a strap [84] for ease of mounting relative to the produce. The strap [84] enables better control of the monitored position of the produce freshness sensor [10] of the present invention relative to the produce [14A, 14B, or 14C]. The produce freshness sensor [10] may also be adhered to, pasted to, packaged with or onto, attached to, or inserted with the produce [14A, 14B, or 14C].

The microprocessor [30] commands the analog front end/LED drivers [50] to power the infrared light guide and LED emitters [61, 62, and 63] to emit energy. The microprocessor [30] looks for energy return at the photo receiver [64]. The emitted energy is either reflected or absorbed by the surface and the underlaying material of the produce [14A, 14B, or 14C]. The reflected energy has a shortened path and is received before the absorbed energy. The energy from each wavelength is received back and captured by the photo receiver [64]. The returned energy is a function of the color plus the water content, and the ethylene in the produce [14A, 14B, or 14C].

POWER MANAGEMENT—Power is provided by a power source [72] (a battery or supercapacitor) and in one preferred embodiment of the produce freshness sensor of the present invention includes energy harvesting. Power usage is critical to prolong the operational time of the produce freshness sensor [10] of the present invention [10]. Data collection and transmission is controlled to minimize the run time and power usage of the components. Low power or sleep modes are much longer than active mode. Wake up and data collection is controlled to look for changes and new data. If no changes are measured the sleep mode is extended until a period of change is encountered and the sleep mode is shortened. Each function has different impacts to quality and rates of change so the amount of on time allotted for each function is prioritized. Temperature changes are more frequent and have a bigger impact to quality so the temperature measuring cycle is the shortest. Ripeness measurement has a relatively slow rate of change and can use a much longer time between on times.

TEMPERATURE MEASUREMENT—The microprocessor [30] wakes up the produce freshness sensor of the present invention [10] at the determine interval. Temperature measurements from the temperature sensor [90] are sent to the microprocessor [30] to be recorded with the time received. The temperature trends are calculated and condensed for sending to the rf transceiver [40] for transmission. Pre-set limits for alerts are stored in the microprocessor [30] and the incoming data is judged against the limits to determine when alerts should be sent. The next wake period is determined from the rate of change.

The value of returned energy from each wavelength is compared against expected values at the period time. The differences between each of the wavelength values are also calculated and used to compare against expected values. The comparisons are made to a data base of many measurements taken with variables that are known to affect the measurements such as the time, distance from the surface, ambient light, and temperature.

An initial baseline is established when the produce freshness sensor [10] is affixed relative to the produce [14A, 14B, or 14C]. The start time and baseline measurements are recorded and stored in the produce freshness sensor [10] of the present invention.

RIPENESS MEASUREMENT—The microprocessor [30] commands the analog front end/LED drivers [50] to power the three infrared light guides and LED emitters [61, 62, and 63] to emit energy and senses energy return at the photo receiver [64]. The time for energy return is used to determine the distance the reflecting surface is from the produce freshness sensor [10]. The distance is used to evaluate the energy signals from the LEDs [61, 62, and 63] since signal intensity or return energy varies with distance. Energy is emitted from the three different wavelength light guides and LED emitters [61, 62, and 63] in sequence. The emitted energy is reflected or absorbed by the surface and the underlaying material of the produce [14A, 14B, or 14C]. Reflected energy has a shortened path and is received before the absorbed energy. The energy from each wavelength is captured by the photo receiver [64]. The amount of energy received is a function of the produce color plus the produce water content, and the amount of ethylene in the produce [14A, 14B, or 14C].

The value of returned energy from each wavelength is compared against expected values as to time. The differences between each of the wavelength values are also calculated and used to compare against expected values. The comparisons are made to a data base of many measurements taken with variables that are known to affect the measurements such as the time, distance from the surface, ambient light, and temperature.

An initial baseline is established when the produce freshness sensor [10] is affixed to the produce [14A, 14B, or 14C]. The start time and baseline measurements are recorded and stored in the produce freshness sensor [10].

The microprocessor [30] is the digital brain of the embedded produce freshness sensor [10]. Thus, choosing the right microprocessor [30] is a critically important design decision. Ideally, the optimum microprocessor [30] offers a very-low-power architecture providing multiple power-down modes for maximizing battery life; good performance for fast, efficient processing fast wake-up times from power-down modes to ensure that the system spends the greatest possible amount of time in a low-power state yet responds quickly to deliver essential system operational capabilities; and a hardware digital signal processor for rapidly and conditioning raw signals, filtering sensor outputs, determining a signal's spectral content, and eliminating false signals.

The microprocessor [30] of choice is a standard low-power ARM Cortex microprocessor with minimal 10 and memory. The microprocessor function can be accomplished with the processor built into the RF transceiver with modified firmware.

The analog front end/LED driver [50] of choice is commercially available from Maxim, Texas Instruments, and Analog Devices among others. The analog front end/LED driver [50] needs to drive the three light guides and emitters [61, 62, and 63] and receive the analog signal from the Phototransistor and provide ADC conversion of the signal for an output via SPI or I2C to the microprocessor. The analog front end/LED driver [50] are commonly used in wearable medical devices and watches.

The light guides and emitters [61, 62, and 63] and photo receiver [64] of choice are commercially available from Osram and Everlight and many others. The infrared 940 nm, red 850 nm, and green 570 nm light guides and emitters [61, 62, and 63] are used in many wearable medical device and watches.

The RF transceiver [40] of choice is used in many IoT devices and available from Nordic, TI, and ST Micro.

Figure 2A:
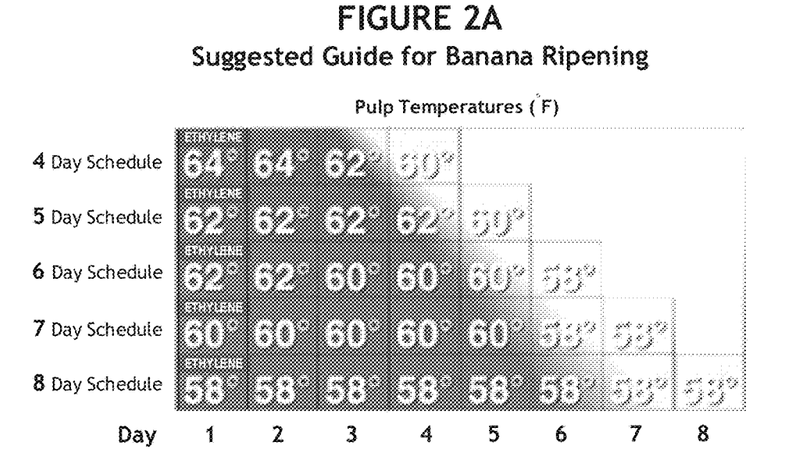
FIG. 2A depicts a daily ripening chart for a "Suggested Guide for Banana Ripening" over a time period from between four to eight-days for use with the produce freshness sensor of the present invention.

FIG. 2A depicts a daily ripening chart for a "Suggested Guide for Banana Ripening" over a period of between 4 and 8 days for use with the produce freshness sensor of the present invention.

The temperatures shown are of the pulp of the produce, not the air temperatures. Proper temperature, humidity, time, air circulation, mature bananas and ethylene are required for ripening. Maintain 100-150 ppm of ethylene until the color breaks. Also, an ethylene chamber as described in the "Super-Ripening Center and Ethyl-Gen II" should be used to hasten ripening. After an initial 24-hour ripening period, the room needs to be vented with a fan on.

Figure 2B:
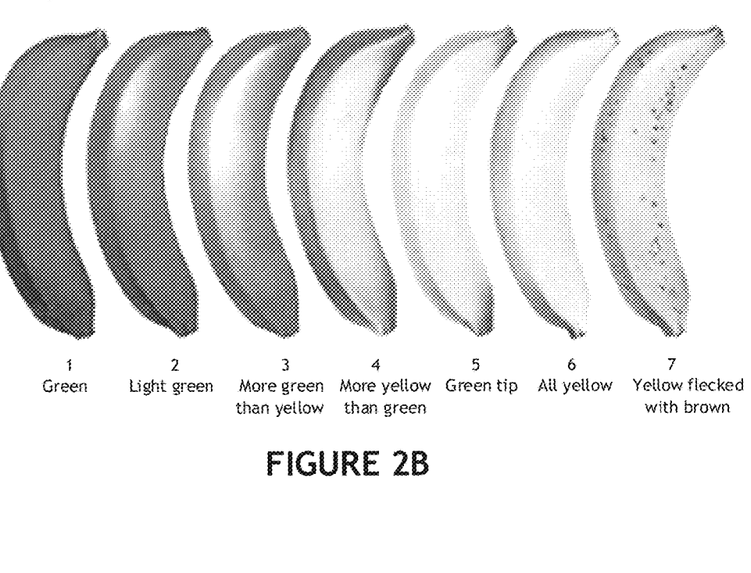
FIG. 2B depicts banana coloring changing with time in seven stages from unripe (stage 1) to ready-to-eat (stage 7), which generally coincides with the "Suggested Guide for Banana Ripening" of FIG. 2A for use with the produce freshness sensor of the present invention.

FIG. 2B depicts banana coloring changing with time in seven stages from unripe (stage 1) to ready-to-eat (stage 7), which generally coincides with the "Suggested Guide for Banana Ripening" of FIG. 2A for use with the produce freshness sensor of the present invention.

Figure 2C:
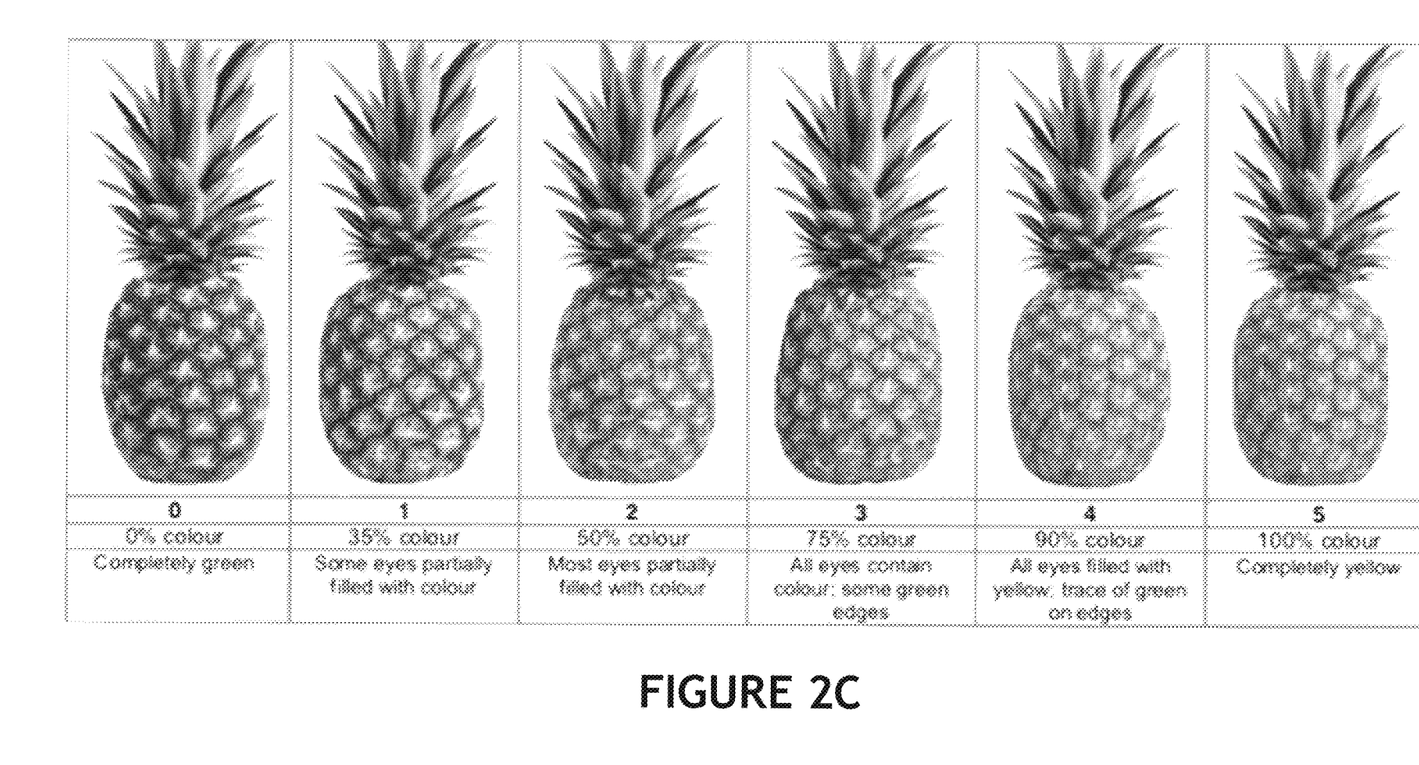
FIG. 2C depicts a pineapple coloring changing chart with time in six stages from unripe completely green (stage 0) to completely yellow and ready-to-eat (stage 5) for use with the produce freshness sensor of the present invention.

FIG. 2C depicts pineapple coloring changing chart with time in six stages from unripe completely green (stage 0) to completely yellow and ready-to-eat (stage 5) for use with the produce freshness sensor of the present invention.

Figure 3A:
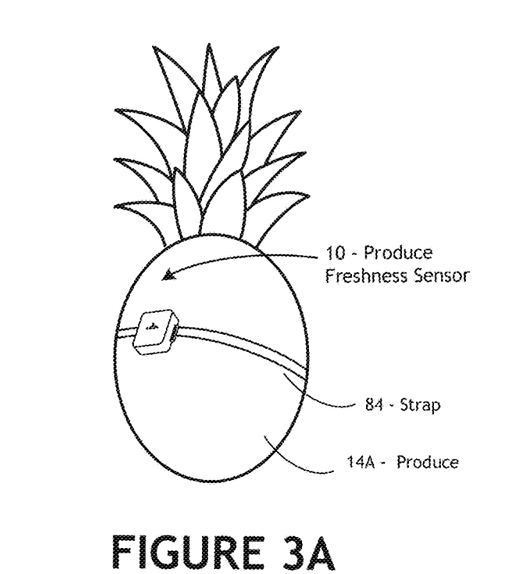
FIG. 3A depicts the produce freshness sensor of FIGS. 1A and 1B affixed to a pineapple.
Figure 3B:
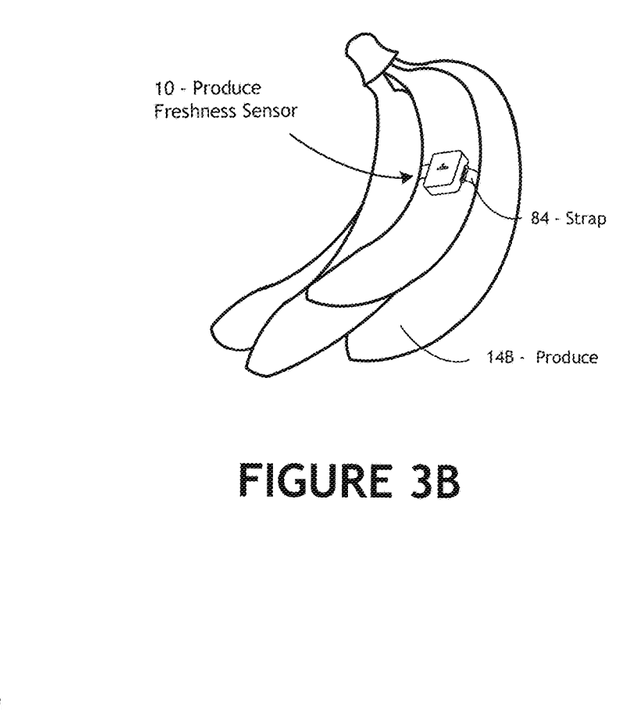
FIG. 3B depicts the produce freshness sensor of FIGS. 1A and 1B affixed to one banana in a bunch of bananas.
Figure 3C:
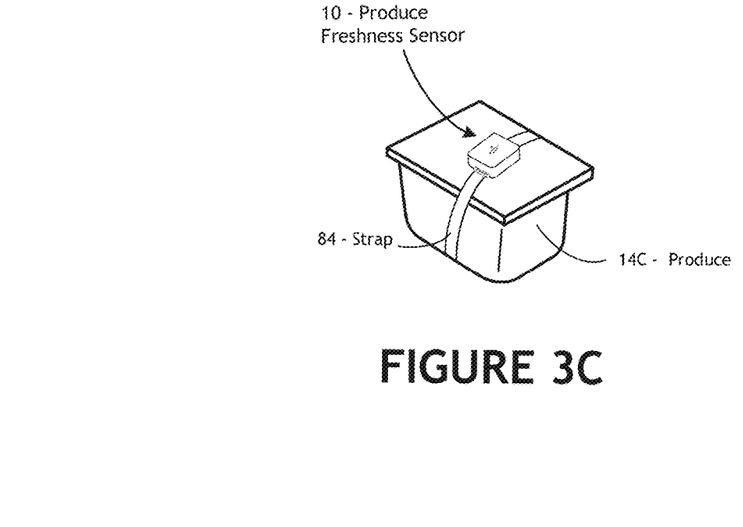
FIG. 3C depicts the produce freshness sensor of FIGS. 1A and 1B affixed to a package of fruit.

FIG. 3A depicts the produce freshness sensor of FIGS. 1A and 1B affixed to a pineapple, FIG. 3B depicts the produce freshness sensor of FIGS. 1A and 1B affixed to one banana in a bunch of bananas, and FIG. 3C depicts the produce freshness sensor of FIGS. 1A and 1B affixed to a package of fruit.

Figure 4:
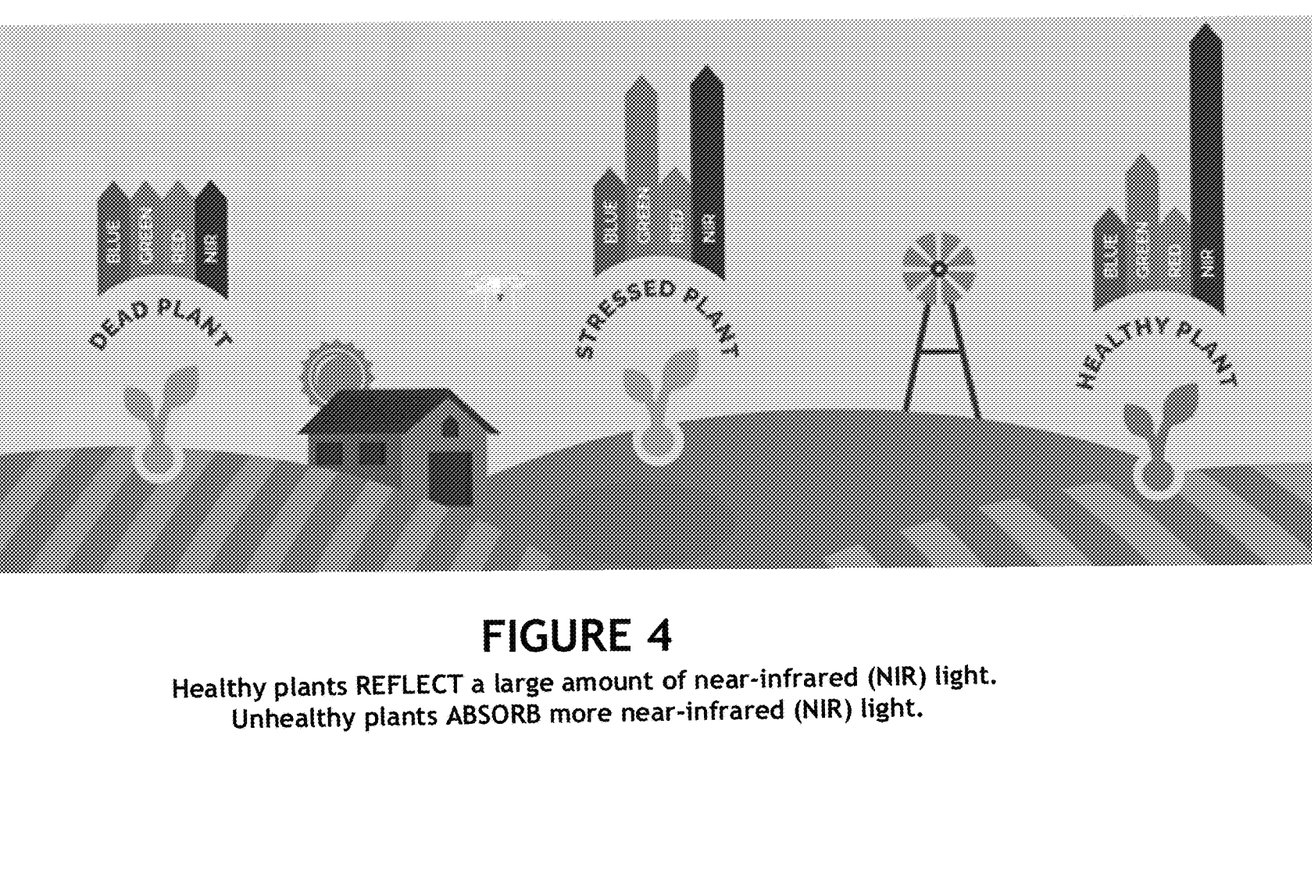
FIG. 4 depicts a simplified depiction of normalized difference vegetation index (NDVI) which is a measurement of plant health based upon the way that a plant reflects light at specific frequencies for use with the produce freshness sensor of the present invention, healthy plants reflecting a large amount of near-infrared light, while unhealthy plants absorbing more near-infrared light.

FIG. 4 depicts a simplified depiction of normalized difference vegetation index (NDVI) which is a measurement of plant health based upon the way that a plant reflects light at specific frequencies for use with the produce freshness sensor of the present invention, healthy plants reflecting a large amount of near-infrared light, while unhealthy plants absorbing more near-infrared light.

Figure 5:
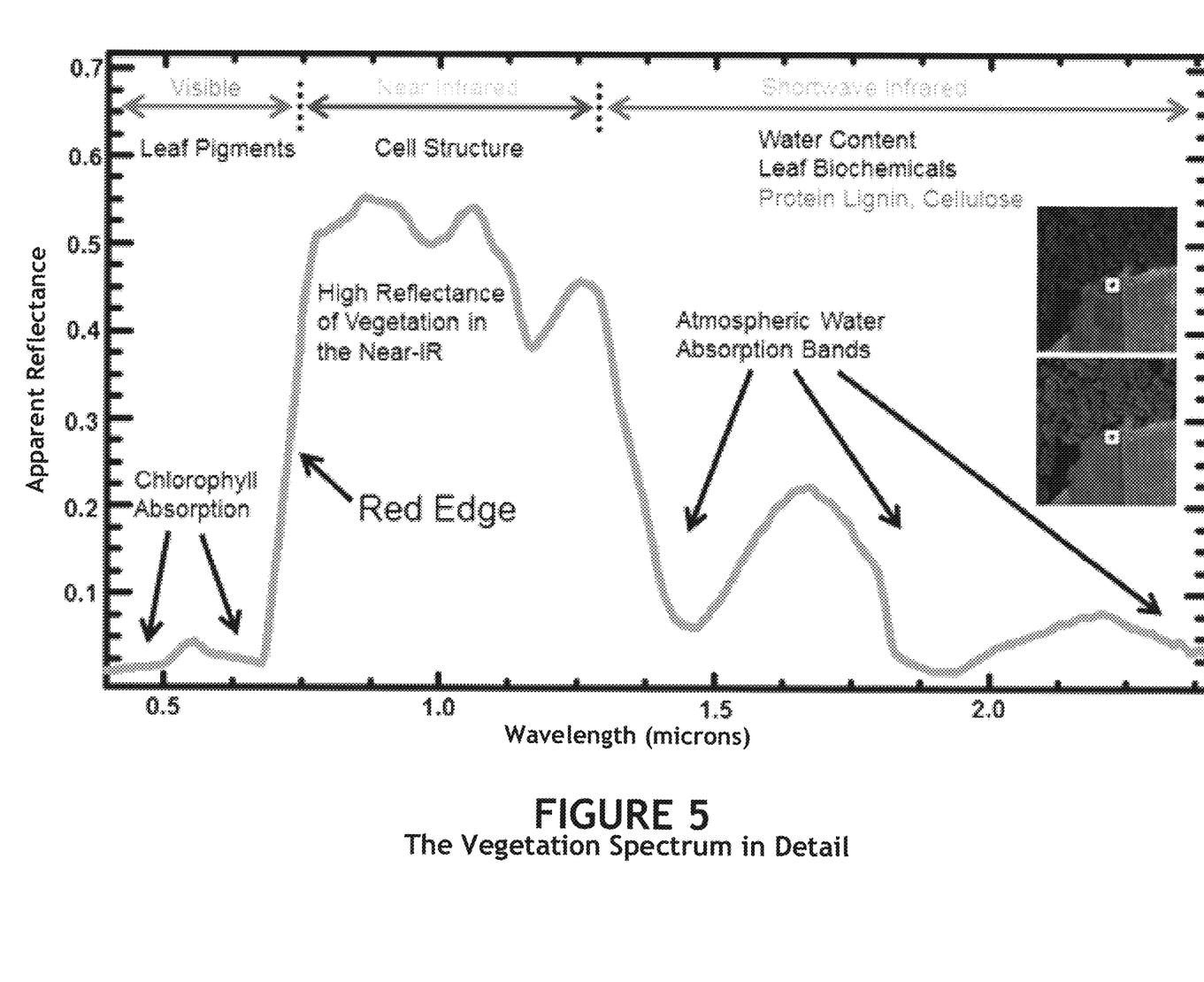
FIG. 5 depicts a chart of the "Vegetation Spectrum in Detail," plotting the "Apparent Reflection" vs. "Wavelength" through the visible wavelength, near-infrared wavelength, and shortwave infrared wavelength for use with the produce freshness sensor of the present invention.

FIG. 5 depicts a chart of the "Vegetation Spectrum in Detail," plotting the "Apparent Reflection" vs. "Wavelength" through the visible wavelength, near-infrared wavelength, and shortwave infrared wavelength for use with the produce freshness sensor of the present invention.

The reflected energy from the visible to the near infrared and into the shortwave infrared wavelengths have specific characteristics that can be used to identify the type of plant and chemical compositions. Spectrometers emit energy or light in a wide band of wavelengths and then filter out the return energy at photo receivers except for specific wavelengths to create plots of the responses for the entire band. Several emitting sources are required to produce the entire band of wavelengths as well as many filters and photo receivers to receive the energy. The equipment to create the full spectrum of energy and measurements are lowering in cost and size but they are still well beyond costs and sizes that enable the equipment to follow the produce through the produce distribution system.

Normalized difference vegetation index (NDVI) is a measurement of plant health based on how a plant reflects light at specific frequencies. Healthy plants reflect a large amount of near infrared (NIR) light, while unhealthy plants absorb more NIR light.

The normalized difference vegetation index (NDVI) is a simple graphical indicator that can be used to analyze remote sensing measurements, often from a space platform, assessing if the target being observed contains live green vegetation.

The NDVI is calculated from these individual measurements as follows:

$$NDVI = \frac{NIR - RED}{NIR + RED}$$

where RED and NIR stand for the spectral reflectance measurements acquired in the red (visible) and near-infrared regions, respectively. These spectral reflectances are themselves ratios of the reflected over the incoming radiation in each spectral band individually, hence they take on values between 0.0 and 1.0. By design, the NDVI itself thus varies between −1.0 and +1.0. NDVI is functionally, but not linearly, equivalent to the simple infrared/red ratio (NIR/VIS). The advantage of NDVI over a simple infrared/red ratio is therefore generally limited to any possible linearity of its functional relationship with vegetation properties (biomass). The simple ratio (unlike NDVI) is always positive, which may have practical advantages, but it also has a mathematically infinite range (0 to infinity), which can be a practical disadvantage as compared to NDVI. Also in this regard, note that the VIS term in the numerator of NDVI only scales the result, thereby creating negative values. NDVI is functionally and linearly equivalent to the ratio NIR/(NIR+VIS), which ranges from 0 to 1 and is thus never negative nor limitless in range.

But the most important concept in the understanding of the NDVI algebraic formula is that, despite its name, it is a transformation of a spectral ratio (NIR/VIS), and it has no functional relationship to a spectral difference (NIR-VIS).

In general, if there is much more reflected radiation in near-infrared wavelengths than in visible wavelengths, then the vegetation in that pixel is likely to be dense and may contain some type of forest. Subsequent work has shown that the NDVI is directly related to the photosynthetic capacity and hence energy absorption of plant canopies. Although the index admits going from −1 to 1, even in more densely populated urban areas the value of normal NDVI is positive, although closer to zero. Negative values are more likely to be disturbed in the atmosphere and some specific materials.

Unmanned aircraft or drones have become a popular and effective tool for monitoring vegetation, analyzing crop health, and predicting yields. Within minutes, overhead imagery of fields can be collected and analyzed to provide actionable data to the grower. If the imagery is accurate and used properly, it can produce significant savings and increased yields for growers. Vegetative Health Indices. In general, most agriculture drone cameras on the market offer a means to create a crop health index map using the photos that are taken by the camera. Most often, the index being displayed is the normalized difference vegetation index (NDVI) or normalized difference red edge (NDRE). These indices are calculated by comparing the amount of light reflected by the crops in various regions of the light spectrum.

Within the electromagnetic spectrum (FIG. 5), the solar-reflected optical spectrum spans a wavelength range from approximately 400 nm to approximately 3000 nm. Of this range, the 400 nm to 2500 nm region is routinely measured using a variety of earth-observing satellite and airborne optical sensors. The optical spectrum is partitioned into four distinct wavelength ranges:

Visible: 400 nm to 700 nm (blue is approximately 475 nm; green is approximately 510 nm; and red is approximately 650 nm)
Near-infrared: 700 nm to 1300 nm
Shortwave infrared 1 (SWIR-1): 1300 nm to 1900 nm
Shortwave infrared 2 (SWIR-2): 1900 nm to 2500 nm The transition from near-infrared radiation to SWIR-1 is marked by the 1400 nm atmospheric water absorption region in which satellites and aircraft cannot acquire measurements. Similarly, the SWIR-1 and SWIR-2 transition is marked by the 1900 nm atmospheric water absorption region.

Figure 6A:
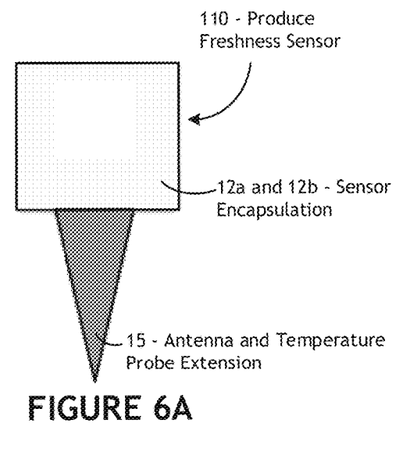
FIG. 6A depicts a front view of the antenna and temperature probe extension of a second preferred embodiment of the produce freshness sensor of the present invention, the components being disposed on a printed circuit board and encapsulated for protection, the temperature probes and antenna are traces on the printed circuit board that extends beyond the encapsulation for improved temperature sensing and wireless transmission.

FIG. 6A depicts a front view of the antenna and temperature probe extension a second preferred embodiment of the produce freshness sensor [110] of the present invention, the components being disposed on a printed circuit board [20] and encapsulated for protection [12], the temperature probes and antenna are traces on the printed circuit board [20] that extends beyond the encapsulation for improved temperature sensing and wireless transmission.

Figure 6B:
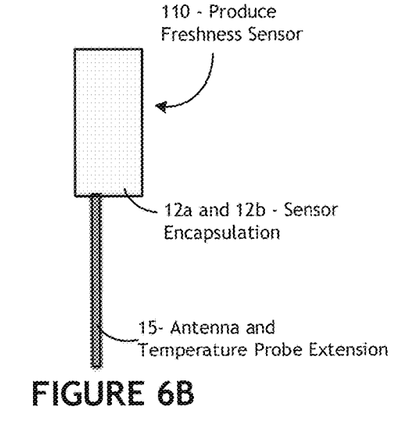
FIG. 6B depicts an end view of the antenna and temperature probe extension of the produce freshness sensor of FIG. 6A, the components being connected on a printed circuit board and encapsulated for protection.

FIG. 6B depicts an end view of the antenna and temperature probe extension of the produce freshness sensor of FIG. 6A, the components being connected on a printed circuit board [20] and encapsulated [12] for protection.

Figures 6C, 6D:
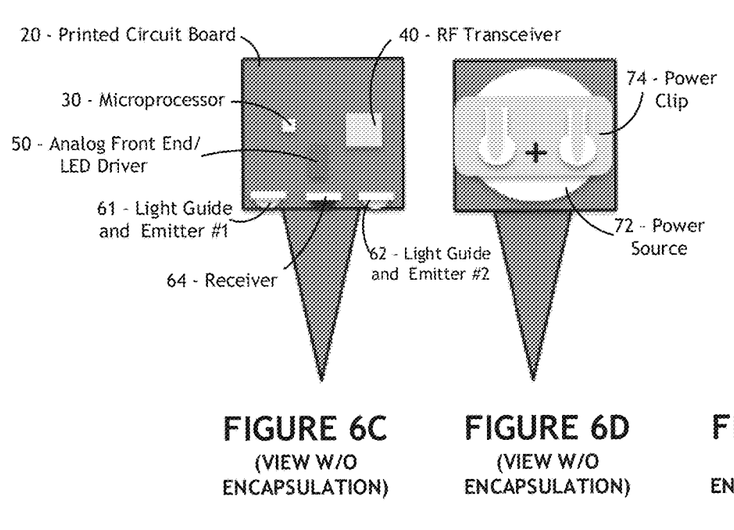
FIG. 6C depicts a front view of the antenna and temperature probe extension of the produce freshness sensor of FIG. 6A, the encapsulation of the printed circuit board being removed, the microprocessor, the analog front end, the rf transceiver, the two emitters and the receiver are shown.
FIG. 6D depicts a back view of the antenna and temperature probe extension of the produce freshness sensor of FIG. 6A, the encapsulation of the printed circuit board being removed, with the power source and the power clip being shown.

FIG. 6C depicts a front view of the antenna and temperature probe extension of the produce freshness sensor [110] of FIG. 6A. The encapsulation [12] of the printed circuit board [20] has been removed, the microprocessor [30], the analog front end [50], the RF transceiver [40], the two emitters [61 and 62] and the receiver [64] are shown.

FIG. 6D depicts a back view of the antenna and temperature probe extension of the produce freshness sensor [110] of FIG. 6A. The encapsulation [12] of the printed circuit board [20] has been removed, and the power source [72] and the power clip [74] are shown.

The power clip [74] secures the coin cell power source [72] and provides connection to the printed circuit board. The power clip [74] is an off-the-shelf part available from suppliers like Keystone Electronics, Corp. Additional cost savings can be achieved with a custom metal stamping.

Figure 6E:
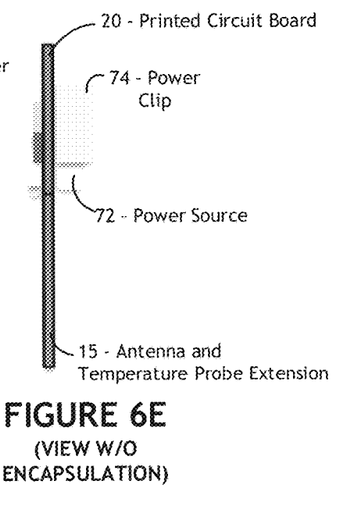
FIG. 6E depicts a back view of the antenna and temperature probe extension of the produce freshness sensor of FIG. 6A, the encapsulation of the printed circuit board being removed, with the power source and the power clip being shown.
Figure 7A:
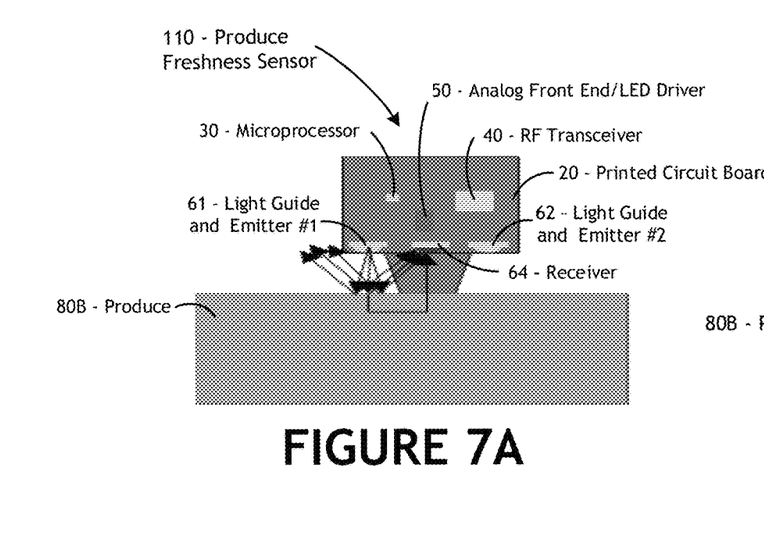
FIGS. 7A and 7B depict a pair of simplified schematics of the produce freshness sensor of FIG. 6A, the microprocessor commanding the LED drivers to power the infrared wavelength #1 LED to emit energy and looking for energy return at the photo receiver, the emitted energy being either reflected or absorbed by the surface and underlaying material of the produce, reflected energy having a shorted path and being received before the absorbed energy, the energy from each wavelength being received back at the photo receiver, the energy returned being a function of the color plus the water content, and ethylene in the produce. The process is repeated with the different wavelength #2 LED.
Figure 7B:
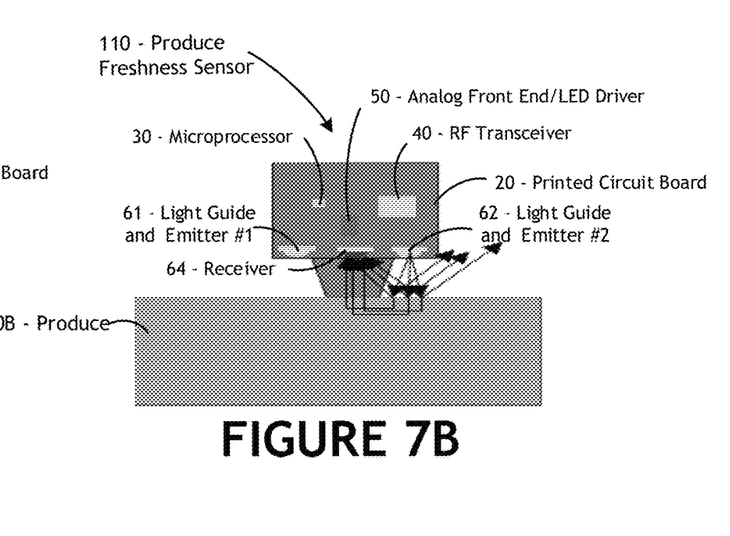

FIG. 6E depicts a back view of the antenna and temperature probe extension of the produce freshness sensor of FIG. 6A. The encapsulation [12] of the printed circuit board has been removed, and the power source [72] and the power clip [74] are shown.

The ability to measure electromagnetic energy at varying wavelengths as it interacts with a material, forms some of the foundation behind remote sensing and spectral science. The physical characteristics of the material cause the electromagnetic energy to be reflected, refracted, or absorbed in a way that is unique to each material. These interactions are measured across discrete sections of the spectrum, that when plotted, form a unique shape that is also known as a material's spectral signature.

Vegetation interacts with solar radiation in a different way than other natural materials. The vegetation spectrum typically absorbs in the red and blue wavelengths, reflects in the green wavelength, strongly reflects in the near infrared (NIR) wavelength, and displays strong absorption features in wavelengths where atmospheric water is present. Different plant materials, water content, pigment, carbon content, nitrogen content, and other properties cause further variation across the spectrum. Measuring these variations and studying their relationship to one another can provide meaningful information about plant health, water content, environmental stress, and other important characteristics. These relationships are often described as vegetation indices (VIs).

Figure 8:
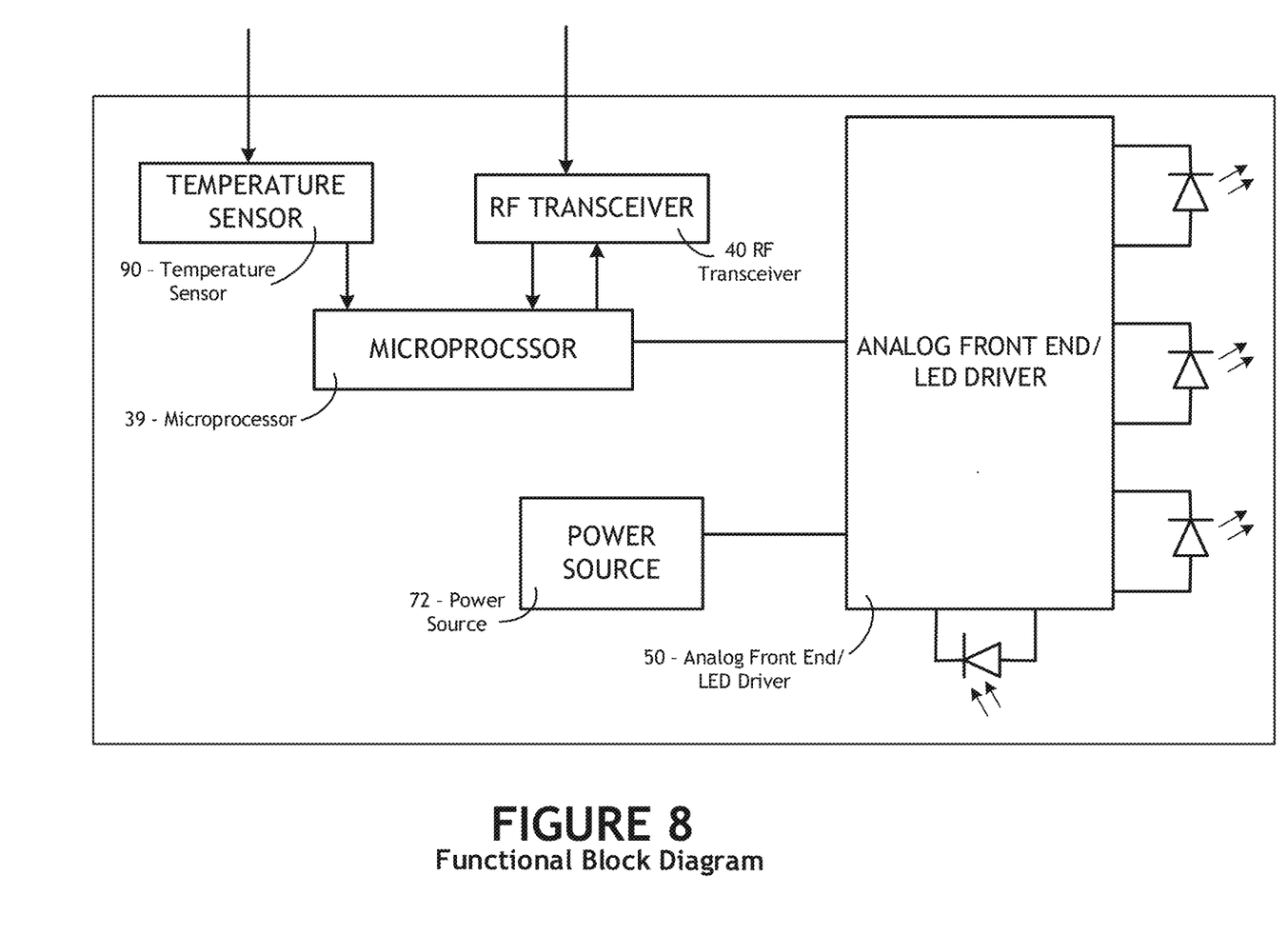
FIG. 8 depicts a simplified functional block diagram of the first preferred embodiment of the produce freshness sensor of FIGS. 1A and 1B, and cooperative relationships of the microprocessor, the rf transceiver, the analog front end/LED driver, temperature sensor, and the power source.

FIG. 8 depicts a simplified functional block diagram of the produce freshness sensor of FIG. 6A, and cooperative relationships of the microprocessor, the temperature sensor, the RF transceiver, the analog front end/LED driver, and the power source.

Figure 9:
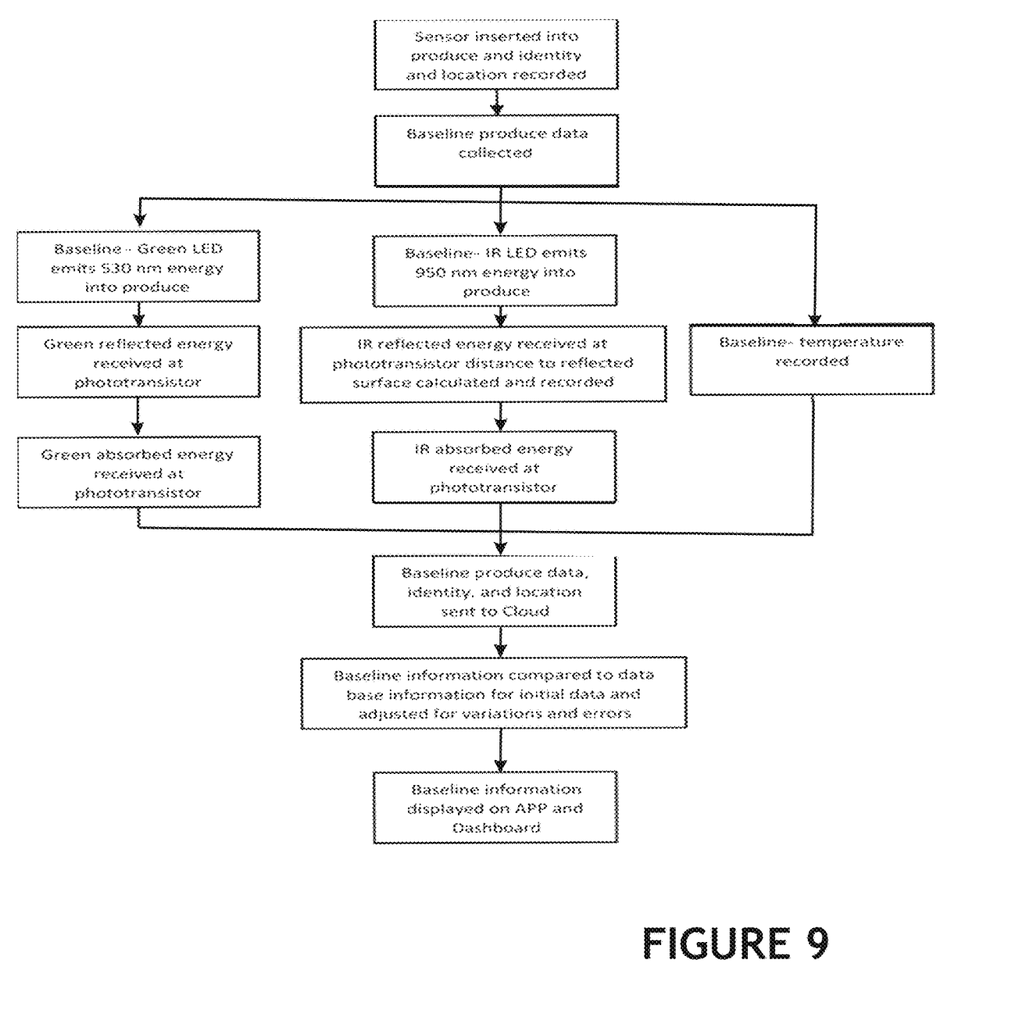
FIG. 9 depicts a simplified logic diagram a third preferred embodiment of the produce freshness sensor of the present invention having but a single light guide and emitter collecting baseline measurements when the produce freshness sensor is affixed to the produce, the start time and baseline measurements being recorded and stored in the produce freshness sensor, baseline produce data, identity, and location being forwarded to the cloud for subsequent comparisons. The green 530 nm wavelength and IR 950 nm wavelength are shown as examples and other wavelengths can be utilized.

FIG. 9 depicts a simplified logic diagram a third embodiment of the produce freshness sensor of the present invention collecting baseline measurements when the sensor is affixed to the produce, the start time and baseline measurements being recorded and stored in the sensor, baseline produce data, identity, and location being forwarded to the cloud for subsequent comparisons.

While the produce freshness sensor of the present invention is operational with a single emitter [61] at a lower cost, the use of a second emitter [62] or even a third emitter [63] provide more information and improved accuracy.

The produce freshness sensor [10] of the present invention provides a lower cost to track temperature and it is the only method that we know of to provide ripeness and location information through the produce distribution system.

In food processing software, traceability systems imply the use of a unique piece of data (e.g., order date or time or a serialized sequence number, generally with a barcode or RFID) which can be traced through the entire production flow, linking all sections of the business, including suppliers and future sales through the supply chain. Messages and files at any point in the produce distribution system can then be audited for correctness and completeness, using the traceability software to find the particular transaction or product within the supply chain.

The size of the produce freshness sensor [10] of the present invention will vary in accordance with the produce [14A, 14B, or 14C]. However, for most applications the printed circuit board [20] measures about 22 mm (wide) and about 22 mm (high) with a thickness of about 6 mm with the antenna and temperature probe extension [15] having a total height of about 50 mm and extending about 28 mm beyond the printed circuit board [20].

Energy harvesting may become a critical element in the future as costs come down. Energy harvesting currently is more expensive than stored energy. The low cost of the produce freshness sensor of the present invention is the major element that will drive acceptance in the marketplace. The cost that the produce freshness sensor of the present invention can be disposed of after a single cycle through the food distribution system. Currently, a 2032-coin cell battery has 200 mAhr for $0.13 which can power the sensor for 90 days or more. This compares favorably to the cost of solar cells, piezo motion, or RF energy harvesting.

Throughout this application, various Patent and Provisional Applications are referenced by number and inventor. The disclosures of these documents in their entireties are hereby incorporated by reference into this specification to more fully describe the state of the art to which this invention pertains.

It is evident that many alternatives, modifications, and variations of the produce freshness sensor of the present invention will be apparent to those skilled in the art in lieu of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

PARTS LIST

10—Produce Freshness Sensor—1st embodiment
11—Temperature Sensor
12a and 12b—Sensor Encapsulation
14A, B, and C—Produce
15—Antenna and Temperature Probe Extension
20—Printed Circuit Board
30—Microprocessor
40—RF Transceiver
50—Analog Front End/LED Driver
61—Light Guide and Emitter #1
62—Light Guide and Emitter #2
63—Light Guide and Emitter #3

64—Light Guide and Receiver
72—Power Source
74—Power Clip
82—Strap Handle
84—Strap
90—Temperature Sensor
110—Produce Freshness Sensor—2<sup>nd</sup> embodiment

The invention claimed is:

1. A method for monitoring freshness of produce, said method comprising:
    providing a produce freshness sensor, said sensor being affixed relative to said produce, said produce freshness sensor including a microprocessor with a power source, said microprocessor employing energy harvesting, data collection and transmission being controlled to minimize run time and power usage of individual components, said produce freshness sensor capturing start time and initial baseline measurements of said produce when said produce freshness sensor is affixed relative to said produce, a start time and subsequent baseline measurements being recorded relative to said initial baseline measurements, said produce freshness sensor providing data in real time relative to location, temperature, and ripeness of said produce; and
    generating data from said produce freshness sensor in real time relative to location, freshness, temperature, and ripeness of said produce as said produce moves through a produce distribution system.

2. The method of claim 1, wherein said power source employs energy harvesting, power usage being critical to prolong operational time of said produce freshness sensor, data collection and transmission being controlled to preserve power usage.

3. The method of claim 2, wherein said microprocessor is awakened at a time interval so that said produce freshness sensor can take one or more intermittent measurements.

4. The method of claim 3, wherein said time interval is predetermined.

5. The method of claim 1, wherein emitted energy from said produce freshness sensor is either reflected or absorbed by an underlaying material of said produce.

6. The method of claim 1, wherein color of said produce is used as a gage of ripeness and chemical composition.

7. The method of claim 1, wherein baseline produce data, identity, and location are forwarded to a cloud for subsequent analysis.

8. A method for monitoring freshness of produce, said method comprising:
    providing a produce freshness sensor, said sensor being affixed relative to said produce, said produce freshness sensor including;
    a microprocessor with a power source;
    an LED driver receiving a command from said microprocessor to power a first LED emitter to emit energy; and
    a photo receiver for capturing wavelength data received back from said first LED emitter;
    said power source employing energy harvesting, data collection and transmission being controlled to minimize run time and power usage of individual components, said produce freshness sensor capturing start time and initial baseline measurements of said produce when said produce freshness sensor is affixed relative to said produce, a start time and subsequent baseline measurements being recorded relative to said initial baseline measurements, said produce freshness sensor providing data in real time relative to location, temperature, and ripeness of said produce; and
    generating data from said produce freshness sensor in real time relative to location, freshness, temperature, and ripeness of said produce as said produce moves through a produce distribution system.

9. The method of claim 8, wherein said microprocessor is awakened at a time interval so that said produce freshness sensor can take one or more intermittent measurements.

10. The method of claim 9, wherein said time interval is predetermined.

11. The method of claim 8, wherein emitted energy from said produce freshness sensor is either reflected or absorbed by an underlaying material of said produce.

12. The method of claim 8, wherein color of said produce is used as a gage of ripeness and chemical composition.

13. The method of claim 8, wherein baseline produce data, identity, and location are forwarded to a cloud for subsequent analysis.

14. A sensor for providing data in real time relative to location, temperature, and ripeness of produce relating to freshness of said produce, said sensor is affixed relative to said produce, said sensor comprising:
    a microprocessor;
    a power source providing power to said microprocessor, said power source employing energy harvesting, data collection and transmission being controlled to minimize run time and power usage of individual components, a start time and subsequent baseline measurements being recorded relative to said initial baseline measurements, said produce freshness sensor providing data in real time relative to location, temperature, and ripeness of said produce;
    an LED driver receiving a command from said microprocessor to power a first LED emitter to emit energy; and
    a photo receiver for capturing wavelength data received back from said first LED emitter;
    wherein said sensor captures a start time and initial baseline measurements of said produce when said produce freshness sensor is affixed relative to said produce, and
    wherein said sensor generates data in real time relative to location, freshness, temperature, and ripeness of said produce as said produce moves through a produce distribution system.

15. The sensor of claim 14, wherein said energy harvesting prolongs operational time of said produce freshness sensor.

16. The sensor of claim 14, wherein said microprocessor, said LED driver, said first LED emitter, and said photoreceiver are mounted on a printed circuit board.

17. The sensor of claim 14, wherein said printed circuit board is encapsulated for protection.

18. The sensor of claim 17, further comprising an antenna, said antenna being traces on said printed circuit board extending beyond said encapsulated printed circuit board.

19. The sensor of claim 14, further comprising a second LED emitter that is cooperatively engaged with said microprocessor, said LED driver, and said photo receiver.

20. A sensor being affixed relative to said produce for providing data in real time relative to location, temperature, and ripeness of said produce relating to freshness of said produce, said sensor comprising:
    a microprocessor;
    a power source providing power to said microprocessor, said power source employing energy harvesting, data collection and transmission being controlled to minimize run time and power usage of individual components, a start time and subsequent baseline measurements being recorded relative to said initial baseline measurements, said produce freshness sensor providing data in real time relative to location, temperature, and ripeness of said produce;

an LED driver receiving a command from said microprocessor to power a first LED emitter to emit energy; and a photo receiver for capturing wavelength data received back from said first LED emitter;

said produce freshness sensor capturing start time and initial baseline measurements of said produce when said produce freshness sensor is affixed relative to said produce, a start time and subsequent baseline measurements being recorded relative to said initial baseline measurements, said produce freshness sensor providing data in real time relative to location, temperature, and ripeness of said produce.

21. The sensor of claim 20, wherein said energy harvesting prolongs operational time of said produce freshness sensor.

22. The sensor of claim 20, wherein said microprocessor, said LED driver, said first LED emitter, and said photoreceiver are mounted on a printed circuit board.

23. The sensor of claim 20, wherein said printed circuit board is encapsulated for protection.

24. The sensor of claim 23, further comprising an antenna, said antenna being traces on said printed circuit board extending beyond said encapsulated printed circuit board.

25. The sensor of claim 20, further comprising a second LED emitter that is cooperatively engaged with said microprocessor, said LED driver, and said photo receiver.

\* \* \* \* \*